United States Patent [19]

McCulloch et al.

[11] Patent Number: 4,922,040

[45] Date of Patent: May 1, 1990

[54] PROCESS FOR EXTRACTING 2,5-DICHLOROTOLUENE FROM ISOMER MIXTURES WITH SODIUM-L ZEOLITE ADSORBENTS

[75] Inventors: Beth McCulloch, Barrington; Anil R. Oroskar, Downers Grove, both of Ill.

[73] Assignee: UOP, Des Plaines, Ill.

[21] Appl. No.: 291,012

[22] Filed: Dec. 28, 1988

[51] Int. Cl.⁵ .................. C07C 17/38; C07C 25/02
[52] U.S. Cl. ............................................... 570/211
[58] Field of Search .................. 570/211; 585/828

[56] References Cited

U.S. PATENT DOCUMENTS

| | | | |
|---|---|---|---|
| 2,985,589 | 5/1961 | Broughton et al. | 210/34 |
| 3,040,777 | 6/1962 | Carson et al. | 137/625.15 |
| 3,216,789 | 11/1965 | Breck et al. | 23/113 |
| 3,422,848 | 6/1969 | Liebman et al. | 137/625.15 |
| 3,706,812 | 12/1972 | DeRosset et al. | 260/674 SA |
| 4,254,062 | 3/1981 | Wambach et al. | 570/211 |
| 4,642,397 | 2/1987 | Zinnen et al. | 568/934 |
| 4,766,262 | 8/1988 | Carra et al. | 570/211 |
| 4,774,371 | 9/1988 | Miwa et al. | 570/211 |
| 4,777,306 | 10/1988 | Kaneshiki et al. | 570/211 |

FOREIGN PATENT DOCUMENTS 2166734 5/1986 United Kingdom .

OTHER PUBLICATIONS

Chen et al., *Chemical Engineering Progress* Feb. 1988, pp. 32–40.

Primary Examiner—Werren B. Lone
Attorney, Agent, or Firm—Thomas K. McBride; John F. Spears, Jr.; Jack H. Hall

[57] ABSTRACT

A process for separating the isomers of dichlorotoluene from a feed mixture of the same. Separation of the isomers is effected by selective adsorption and desorption and is susceptible to various flow schemes for performing continuous adsorptive separations. The process uses an L-type adsorbent having alkali metal cations, or mixtures thereof as cations and a desorbent containing 1,2-dichlorobenzene or chlorobenzene alone or either admixed with saturated aliphatic hydrocarbons having less than 9 carbon atoms.

16 Claims, 3 Drawing Sheets

PROCESS FOR EXTRACTING 2,5-DICHLOROTOLUENE FROM ISOMER MIXTURES WITH SODIUM-L ZEOLITE ADSORBENTS

BACKGROUND OF THE INVENTION

1. FIELD OF THE INVENTION

The field of art to which this invention pertains is the solid bed adsorptive separation of dichlorotoluene (DCT) isomers. More specifically, the invention relates to a process for extracting the 2,5-isomer of dichlorotoluene (2,5-DCT) from mixtures of DCT isomers employing as the adsorbent L zeolites containing alkali metal cations.

2. BACKGROUND INFORMATION

The individual isomers of dichlorotoluene are useful in a variety of reactions, e.g., as intermediates for making pesticides, pharmaceuticals, peroxides, dyes, etc. The dichlorotoluene isomers are normally prepared by the non-catalytic nuclear chlorination of chlorotoluene in various solvents. The chlorinating agent comprises certain Lewis acid halides, e.g., hydrogen chloride in both liquid and vapor phase systems. The direct chlorination of ortho-chlorotoluene produces a mixture of 2,3-DCT, 2,4-DCT, 2,5-DCT and 2,6DCT while the direct chlorination of para-chlorotoluene produces 3,4-DCT and 2.4-DCT. The direct chlorination of toluene produces a mixture of 2,3-, 2,4-, 2,5-, 2,6-, and 3,4-DCT.

Separation of 2.5-DCT from the other isomers of dichlorotoluene by conventional distillation techniques is difficult due to the close boiling point range of these isomers. The following table shows the boiling points of the 2,4-DCT, 2,5-DCT, 3,5-DCT and 2,6-DCT isomers to be separated by less than 1° C.

TABLE 1

| DCT Isomer | Boiling Point (°C.) |
| --- | --- |
| 2,3-DCT | 208.3 |
| 3,4-DCT | 208.9 |
| 2,4-DCT | 201.1 |
| 2,5-DCT | 201.8 |
| 2,6-DCT | 200.6 |
| 3,5-DCT | 201.2 |

While it is possible to separate 2,3-DCT by distillation from the isomer mixture produced by the process of direct chlorination of o-chlorotoluene referred to above, the utilities duty of the overall process can be reduced substantially by our process by separating and recovering 2,5-DCT as the extract of a first adsorptive separation and distilling the raffinate containing 2,3-, 2,4- and 2,6-DCT to remove 2,3-DCT from the lowered volume rather than from the original feed. The remaining raffinate components can then be separated by a further adsorptive stage using the same adsorbent and conditions. This invention simplifies the separation procedure by providing an effective adsorptive separation method for recovering 2,5-DCT.

Crystalline alumina-silicates are commonly used in the separation art to perform adsorptive separations. The use of X or Y zeolites to separate individual isomers of dichlorotoluene is disclosed in U.S. Pat. No. 4,254,062. It is noted that 2,6-DCT is preferentially adsorbed onto the sodium or calcium form of X or Y zeolites, while the barium form or mixed barium-calcium form preferentially adsorb 2,4-DCT.

U.S. Pat. No. 4,774,371 discloses a static test for determining which dichlorotoluene isomers are adsorbed in the presence of other materials. For example, 2,6-dichlorotoluene is selectively adsorbed on X- or Y-type faujasite zeolites when a substituted benzene compound, preferably toluene, xylene, chlorotoluene or trimethylbenzene is present. Also, 3,5-DCT can be separated as the extract component when the substituted benzene compound is 1,2,4-trimethylbenzene or 2-chloro-p-xylene.

U.S. Pat. No. 4,766,262 and Japanese Public Disclosure No. 149636/87 dated July 3, 1987 disclose a selective adsorptive separation of dichlorotoluene isomers with a mordenite molecular sieve and an acid-treated mordenite type zeolite, respectively. In the former, 2,6-DCT is selectively adsorbed and recovered in the extract while in the latter 2,6-dichlorotoluene is non-adsorbed and recovered in the raffinate in a rejective-type separation. In 4,766,262, there appears to be little separation between the 2,5-, 2,4- and 3,4-isomers, although selectivity is noted as between the 2,6-DCT and 2,5-DCT isomers. In Examples 3 thru 5, and 9 and 10 (in vapor phase) of the patent, 2,5-DCT is selectively adsorbed with respect to 2,6-DCT, but it appears that 2,4-DCT is coextracted with the 2,5-DCT. In Examples 11 and 12, in liquid phase, 2,6-DCT is selectively adsorbed with respect to 2,5-DCT.

Japanese Public Disclosure No. 112034/86, dated May 30, 1986, and U.S. Pat. No. 4,777,306 disclose the separation of dichlorotoluene isomers on a ZSM-5 type zeolite. The adsorbed isomers can be desorbed with an eluent which may be a substituted and/or halogenated momocyclic or polycyclic aromatic compound, according to Japanese Public Disclosure 112034/86. In U.S. Pat. No. 4,777,306, 2,6-DCT is separated as the non-adsorbed isomer from the adsorbed isomers by a rejective separation process. In a comparative example in U.S. Pat. No. 4,777,306, it was disclosed that K-L zeolite had no adsorptive or separating effect.

Methods for forming the crystalline powders into agglomerates are also known and include the addition of an inorganic binder, generally a clay comprising a silicon dioxide and aluminum oxide, to a high purity zeolite powder in wet mixture. The blended clay zeolite mixture is extruded into cylindrical type pellets or formed into beads which are subsequently calcined in order to convert the clay to an amorphous binder of considerable mechanical strength. Clays of the kaolin type, water permeable organic polymers and silica may also be used as binders.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRossett U.S. Pat. No. 3,706,812) to commercial scale in flow rates from a few cc per hour to many thousands of gallons per hour.

The functions and properties of adsorbents and desorbents in the chromatographic separation of liquid components are well-known, but for reference thereto, Zinnen et al. U.S. Pat. No. 4,642,397 is incorporated herein.

It has now been discovered that L-type zeolites exchanged with sodium, potassium or lithium cations or mixtures thereof at cation, exchange sites are suitable adsorbents for the separation of 2,5-DCT from other isomers of DCT, provided certain conditions in the chromatographic separation process are maintained. Two parameters that must be controlled in the process are the water concentration of the adsorbent and temperature of the process.

SUMMARY OF THE INVENTION

In brief summary, the invention is a process for separating the isomers of dichlorotoluene from a feed mixture comprising a mixture of the isomers. The process comprises contacting the isomers at adsorption conditions with an adsorbent comprising an L zeolite containing an alkali metal cation or combinations thereof at cation exchange sites. After contact with the adsorbent, the unadsorbed portion of the feed is removed and the adsorbed component is recovered using a desorbent comprising chlorobenzene or 1,2-dichlorobenzene and especially in admixture with a diluent comprising a saturated aliphatic hydrocarbon. Especially preferred as diluents are saturated aliphatic hydrocarbons having less than 9 carbon atoms.

In a more specific embodiment, in which the feed comprises the 2,3-, 2,4-, 2,5- and 2,6-DCT isomers, a process scheme is set forth so as to separate, in substantially higher concentration than the feed, each of the isomers present. Specifically, 2,5-DCT is recovered as extract from the first adsorption stage. The first stage raffinate contains 2,3- 2,4- and 2,6-DCT. In the second adsorption stage, the first stage raffinate is contacted with the same adsorbent-desorbent combination as the first stage, following distillation to remove 2,3-DCT from the first stage raffinate; 2,6-DCT is the extract product and 2,4-DCT is the raffinate product from the second adsorption stage.

In the specific two-stage embodiment just referred to, the process for the separation of dichlorotoluene isomers from a feed mixture comprising the 2,3-, 2,4-, 2,5- and 2,6-DCT isomers comprises contacting said feed mixture, at adsorption conditions, with a first adsorbent comprising an L-type zeolite having cations selected from the group consisting of sodium, lithium or potassium ions or mixtures thereof at cation exchange sites, selectively adsorbing one or more of the adsorbable isomers, removing the less strongly adsorbed or as sometimes referred to herein, relatively non-adsorbed, portion of the feed mixture from contact with said first adsorbent and thereafter recovering said adsorbed dichlorotoluene isomers by contacting said first adsorbent containing adsorbed dichlorotoluenes, at desorption conditions, with a first desorbent material comprising from 10 to 50% (vol.) chlorobenzene and from 90 to 50% (vol.) of a saturated aliphatic hydrocarbon having less than 9 carbon atoms, said non-adsorbed portion comprising 2,4-DCT in higher concentration (excluding desorbent) than in said feed and substantially lower concentrations of the less strongly adsorbed isomers and said adsorbed isomers comprising a substantially higher concentration of 2,5-DCT than in said feed, recovering said 2,3-DCT from said non-adsorbed portion by fractionation following the removal of said non-adsorbed portion from contact with said first adsorbent and contacting the remaining 2,4- and 2,6DCT isomers of said less strongly adsorbed portion with a second adsorbent from the same group as the first adsorbent, removing a second non-adsorbed portion richer in 2,4-DCT from contact with said second adsorbent and thereafter recovering 2,6-DCT from said second adsorbent by contacting said second adsorbent at desorption conditions with a second desorbent selected from the same group as the first mentioned desorbent.

Other embodiments of the present invention encompass specific feed mixtures, desorbent compositions, flow schemes and operating conditions, all of which are hereinafter disclosed in the following discussion of the present invention.

Preferred feed mixtures for this process contain substantial quantities of the 2,3-, 2,4-, 2,5- and 2,6-isomers of dichlorotoluene obtained by chlorination of highly pure o-chlorotoluene.

To separate the 2,5-DCT isomer from a mixture of dichlorotoluene isomers in accordance with the present invention, the mixture is contacted with the previously mentioned class of adsorbents and the 2,5-isomer is selectively adsorbed and retained by the adsorbent while the other relatively unadsorbed isomers are removed from the interstitial void spaces between the particles of adsorbent in the surface of adsorbent. The adsorbent containing the more selectively adsorbed isomer is referred to as a "rich" adsorbent. The more selectively adsorbed isomer is then recovered from the rich adsorbent by contacting the rich adsorbent with a desorbent material.

In the process of this invention, it has been found that particular desorbent materials, comprising mixtures of chlorobenzene or 1,2-dichlorobenzene and saturated aliphatic hydrocarbons, will increase overall selectivity in the adsorptive separation of dichlorotoluene isomers with the adsorbents herein described. Of the possible saturated aliphatic hydrocarbons which may be used in the desorbents, those having less than 9 carbon atoms are most useful due to their lower boiling point properties. Of these hydrocarbons, $C_4$–$C_8$ are preferred. The particularly preferred hydrocarbon is n-heptane. Moreover, the preferred desorbents will contain 10–50 vol. % of chlorobenzene and 50–90 vol. % of the hydrocarbon. A particularly preferred desorbent is a mixture of 20 vol. % chlorobenzene and 80 vol. % n-heptane.

DETAILED DESCRIPTION OF THE INVENTION

Figure 1:
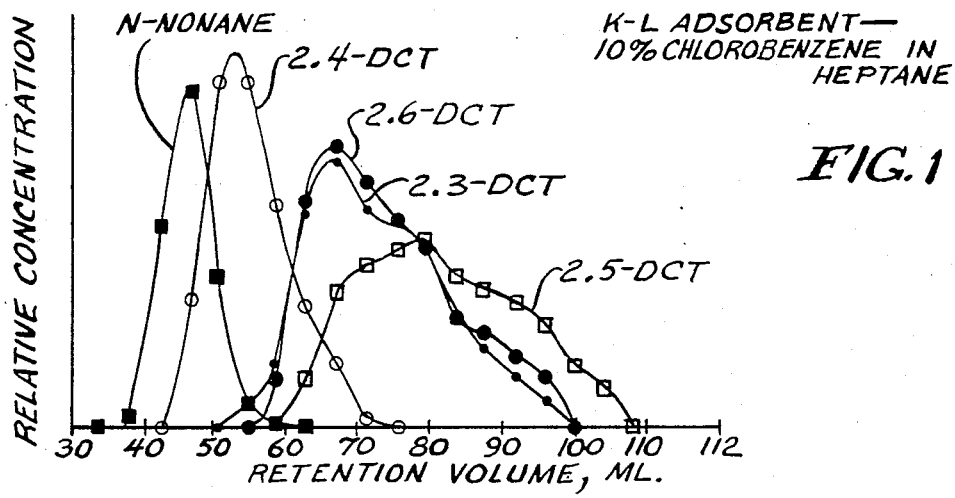
FIGS. 1–5 are chromatographic traces representing the separations of Examples I and II with K-L zeolite and chlorobenzene at various dilutions as desorbent.

Adsorbents to be used in the process of this invention will comprise specific crystalline aluminosilicates or molecular sieves, namely L zeolites. The L zeolite structure contains alumina and silica tetrahedra which are intimately connected with additional oxygen atoms in a network to form one-dimensional channels. The tetrahedra are crosslinked by the sharing of oxygen atoms with spaces between the tetrahedra occupied by water molecules prior to partial or total dehydration of this zeolite. The dehydration of the zeolite results in crystals interlaced with cells having molecular dimensions and thus the crystalline aluminosilicates are often referred to as "molecular sieves". In the present invention, the water content of the adsorbent, based on loss on ignition (L.O.I.), is from 0.1 to 20% (wt.), preferably 0.5% (wt.).

The L zeolite in the hydrated or partially hydrated form may be represented in terms of moles of oxides as in Formula 1 below:

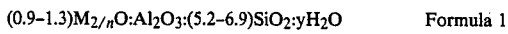

$$(0.9-1.3)M_{2/n}O:Al_2O_3:(5.2-6.9)SiO_2:yH_2O \qquad \text{Formula 1}$$

where M designates at least one exchangeable cation as referred to above, n is the valence of M and y may be any value from 0 to about 9. It is preferred to synthesize the potassium form of the L-type zeolite since the reactants to make this form are readily available and generally water soluble. Thus, the as-made form of the L zeolite is referred to as potassium-L, or K-L, zeolite. L-zeolite is characterized by planar 12-ring pores aligned to produce one-dimensional channels, linked to each other by small pore openings which will not admit water molecules. A minor two-dimensional pore system also exists, parallel to the aforesaid channels. For further description of the L-zeolites, see Breck, *Zeolite Molecular Sieves Structure, Chemistry, and Use*, John Wiley & Sons, New York, 1974, pp 113–6, 156 and Breck et al U.S. Pat. No. 3,216,789, which is incorporated herein by reference.

Although the separation can be accomplished with K-L zeolite adsorbent, we prefer the potassium ions partially or, to the fullest extent possible, exchanged by sodium or lithium. The most preferred mixed NaK-L zeolite contains from 0.5 to 3 wt. % sodium and about 12.2 to about 8 wt. % potassium. Up to about 13% potassium is present in the L zeolite in the as-formed state. Fully exchanged, i.e., to the maximum extent possible, L zeolite is calculated to contain about 3.0% sodium and 8.0% potassium.

The adsorbent may be supported by an inorganic matrix material such as silica, titania, or alumina or mixtures thereof, or compounds, such as clays, which material is present in intimate mixture with the small particles of the zeolite material. This matrix material, or binder, typically in amounts ranging from 2–25 wt. %, aids in forming or agglomerating the particles and may be an adjunct of the manufacturing process for zeolite, (for example, intentionally incomplete purification of either zeolite during its manufacture) or it may be added to relatively pure zeolite. Normally, the adsorbent will be in the form of particles such as extrudates, aggregates, tablets, macrospheres or granules having a desired particle size range. The typical adsorbent will have a particle size range of about 16–60 mesh (Standard U.S. Mesh).

Although it is not clear what properties of the adsorbent are responsible for the separation of dichlorotoluene isomers herein described, it appears that it cannot be attributed to pore size selectivity alone. Since the isomers being separated are of similar size, it appears that steric factors as well as electrostatic attraction action may play an important role in the separation. A possible explanation is that the steric factors may be the most important factors since the 2,5-DCT is the most strongly adsorbed isomer on the L zeolite (except for 2,3-DCT, which is coextracted), whereas X and Y faujasite-type zeolites are selective for 2,6-DCT. L zeolites exhibit a one-dimensional channel structure whereas faujasite-type zeolites are comprised of three-dimension cages. It is theorized that this difference in structure of the L zeolite compared to faujasite-type zeolites is responsible for the unexpected performance of L zeolite in separating dichlorotoluenes.

We have found that L zeolites with potassium cations at the cation exchange sites or a combination of sodium or lithium and potassium cations and amorphous binders posses the selectivity and other necessary requirements for use in our process; however, a potassium L type zeolite partially exchanged with sodium is particularly preferred.

In this process, and particularly the preferred continuous simulated moving bed process, the desorbent must be selected to satisfy the following criteria: First, the desorbent material should displace an extract component from the adsorbent with reasonable mass flow rates without itself being so strongly adsorbed in a following adsorption cycle. Secondly, the desorbent material must be compatible with the particular adsorbent and the particular feed mixture. More specifically, it must not reduce or destroy the critical selectivity of the adsorbent for an extract component with respect to a raffinate component. The desorbent should additionally be easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high nor would the desorbent material be available for reuse in the process. It is, therefore, contemplated that any desorbent material used in this process will preferably have a substantially different average boiling point than that of the feed mixture, i.e., more than about 5° C. difference, to allow separation of at least a portion of desorbent material from feed components in the extract and raffinate streams by simple fractional distillation, thereby permitting reuse of desorbent material in the process. Finally, desorbent materials should also be materials which are readily available and reasonable in cost. However, a suitable desorbent or desorbents for a particular separation with a specific adsorbent are not always predictable. In the preferred isothermal, isobaric, liquid-phase operation of the process of my invention, I have found that desorbent material comprising 10–50 vol. % chlorobenzene and a saturated aliphatic hydrocarbon having less than 9 carbon atoms will result in increased selectivity for the adsorbed 2,5-DCT isomer when used with the above discussed adsorbents.

Feed mixtures which can be separated in the process of this invention result from the chlorination of ortho-chlorotoluene which produces the following mixture isomers: 2,3-, 2,4-, 2,5- and 2,6-dichlorotoluene. The feed mixture should contain as little 3,4-DCT as possible, since 3,4-DCT is also adsorbed and desorbed by the desorbents described herein. Since 3,4-DCT is formed from the chlorination of para-chlorotoluene, the p-chlorotoluene in the o-chlorotoluene feed preparation should be kept as low as possible. A highly advantageous process for removing p-chlorotoluene from the o-chlorotoluene feed to the chlorination process is disclosed in McCulloch copending application, Ser. No. 290,794, filed Dec. 28, 1988, in which the same adsorbent and desorbent system disclosed herein have been used thereby enabling the purification of the o-chlorotoluene in the same equipment used in the instant process, achieving substantial capital and inventory cost savings.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 110° C. to about 200° C., with about 150° C. to about 180° C. being preferred and a pressure sufficient to maintain liquid-phase, ranging from about atmospheric to about 500 psig with from about atmospheric to about 200 psig usually being adequate. Desorption conditions will include the same range of temperatures and pressures as used for adsorption conditions. Although some increase within the above range was noted, the temperature is believed to be otherwise critical.

At least a portion of the extract stream, which contains the concentrated 2,5-DCT product, and preferably at least a portion of the raffinate stream, from the separation process are passed to separation means, typically fractionators or evaporators, where at least a portion of desorbent material is separated to produce an extract product and a raffinate product, respectively.

A dynamic testing apparatus is employed to test various adsorbents with a particular feed mixture and desorbent material to measure the adsorption characteristics of retention, capacity and exchange rate. The apparatus consists of a helical adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect qualitatively, or determine quantitatively, one or more components in the effluent stream leaving the adsorbent chamber. A pulse test, performed using this apparatus and the following general procedure, is used to determine data, e.g., selectivity, for various adsorbent systems. The adsorbent is placed in a chamber and filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent material is injected for a duration of several minutes. Desorbent material flow is resumed, and the tracer and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, adsorbent performance can be rated in terms of void volume, net retention volume (NRV) for an extract or a raffinate component, the rate of desorption of an extract component from the adsorbent and selectivity. The net retention volume of an extract or a raffinate component may be characterized by the distance between the center of the peak envelope of the extract or raffinate component and the center of the peak envelope of the tracer component (void volume) or some other known reference point. Gross retention volume (GRV) is the distance between the center of a peak envelope and the zero abscissa and measured as total ml. of desorbent material pumped during this interval. NRV is also the difference between the respective GRVs and the GRV of the tracer. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. Selectivity, $\beta$, is determined by the ratio of the net retention volumes of the more strongly adsorbed component to each of the other components.

The examples shown below are intended to further illustrate the process of this invention without unduly limiting the scope and spirit of said process. The examples present test results for various adsorbent and desorbent materials when using the above dynamic testing apparatus.

EXAMPLE I

In this experiment, two pulse tests, as described above, were performed to evaluate the advantage of the present invention in separating 2,5-dichlorotoluene from a feed containing chlorotoluene isomers: 2,3-DCT, 2,4-DCT, 2,5-DCT and 2,6-DCT.

Figure 2:
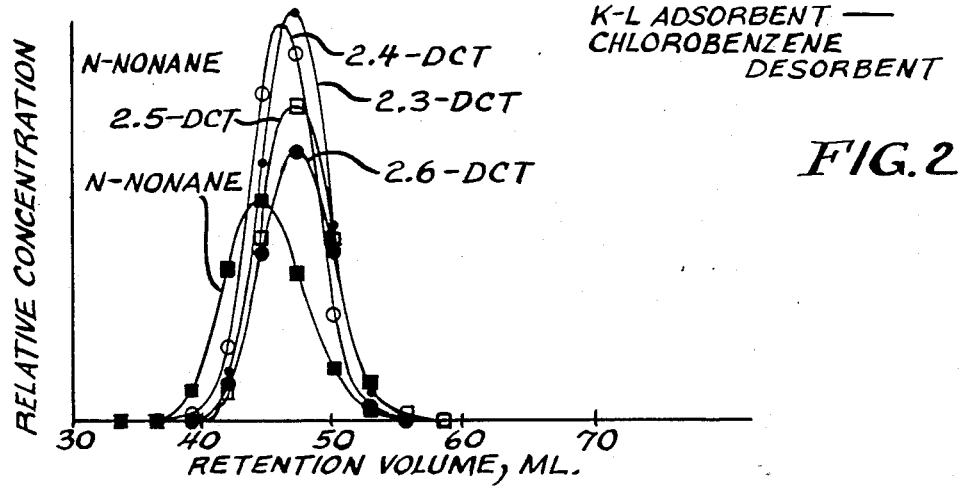

In the first pulse test, the column was filled with 70 cc of a type L zeolite having potassium cations at cation exchange sites and maintained at a temperature of 150° C. and a pressure sufficient to provide liquid-phase operations. The feed mixture employed for this test containing 5 vol. % of each isomer and 4% (vol.) n-nonane. The desorbent material was 10% chlorobenzene in n-heptane ($nC_7$). The apparatus conditions and feedstock were the same for the second test with the only differences being in the use of a desorbent material of 100 vol. % chlorobenzene and a feed containing 4% of each isomer and 2% (vol.) n-nonane. The operations taking place for each test were as follows. The desorbent material was run continuously at a nominal liquid hourly space velocity (LHSV) of 1 which amounted to about 1.4 cc per minute flow rate of desorbent. At some convenient time interval, the desorbent was stopped and the feed mixture was run for a 3.6 minute interval at a rate of 1.4 cc per minute. The desorbent stream was then resumed at 1 LHSV and continued to pass into the adsorbent column until all of the feed components had been eluted from the column as determined by observing the chromatograph generated by the effluent material leaving the adsorption column. The sequence of operations usually takes about an hour. The 3.6 minute pulse of feed and subsequent desorption may be repeated in sequence as often as is desired. The chromatograph tracings obtained from Pulse Tests 1 and 2 are shown in the attached FIGS. 1 and 2, respectively. The tracings of FIG. 1, representing Test 1, show the separation of 2,5-dichlorotoluene, the selectively adsorbed component from the remaining isomers. FIG. 2 shows no separation, using the potassium exchanged L zeolite, takes place with 100% chlorobenzene desorbent. The results are also set forth in the following table of retention values and selectivities ($\beta$).

TABLE 1

| Sample No. | Desorbent | Component | GRV | NRV | BETA ($\beta$) |
|---|---|---|---|---|---|
| I-1 | 10% dichlorobenzene | Nonane | 45.2 | 0.0 | tracer |
|  | 90% n-heptane | 2,4-DCT | 53.5 | 8.3 | 4.28 |
|  |  | 2,6-DCT | 70.9 | 25.7 | 1.38 |
|  |  | 2,5-DCT | 80.6 | 35.4 | Reference |
|  |  | 2,3-DCT | 71.1 | 25.9 | 1.37 |
| I-2 | 100% chlorobenzene | Nonane | 44.9 | 0.0 | tracer |
|  |  | 2,4-DCT | 46.4 | 1.5 | 1.80 |
|  |  | 2,6-DCT | 47.6 | 2.8 | 0.99 |
|  |  | 2,5-DCT | 47.6 | 2.7 | Reference |
|  |  | 2,3-DCT | 47.1 | 2.3 | 1.20 |

EXAMPLE II

Figure 3:
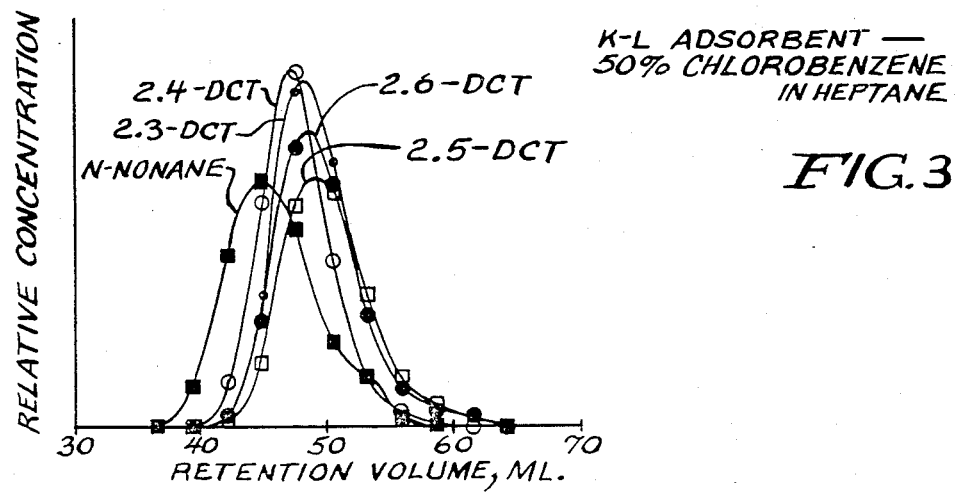
Figure 4:
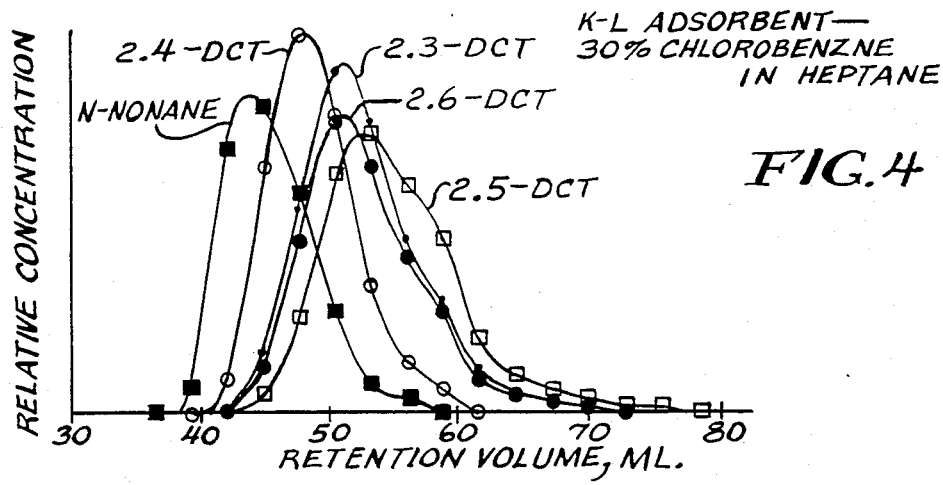
Figure 5:
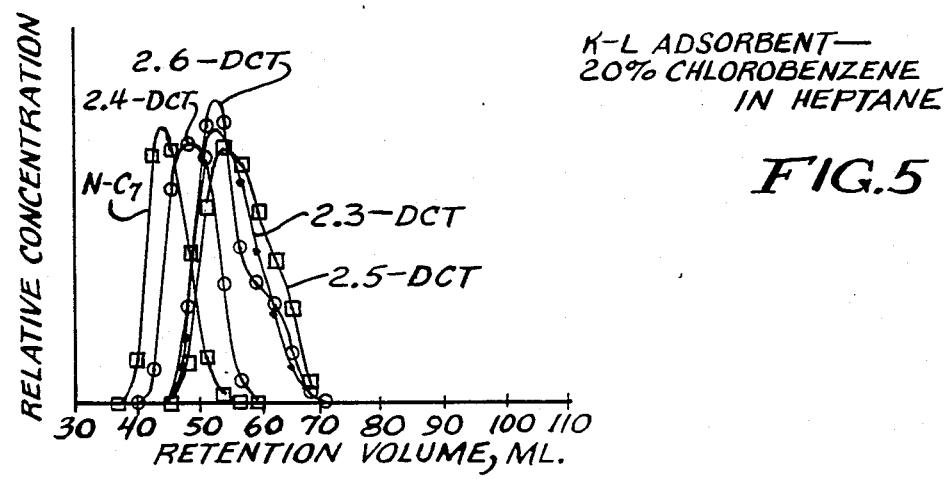

To demonstrate the effect of dilution of chlorobenzene on the adsorptive separation process, three additional pulse tests were performed with a K-L zeolite on a feed consisting of 4 vol. % each of 2,3-, 2,4-, 2,5- and 2,6-DCT and 2% nonane under the same conditions of Example I. In this example, the desorbent material for the three samples consisted of concentrations of chlorobenzene in n-heptane, 50%, 30% and 20%, respectively. The results of this pulse test are presented in Table 2 and FIGS. 3, 4 and 5, respectively.

TABLE 2

Figure 6:
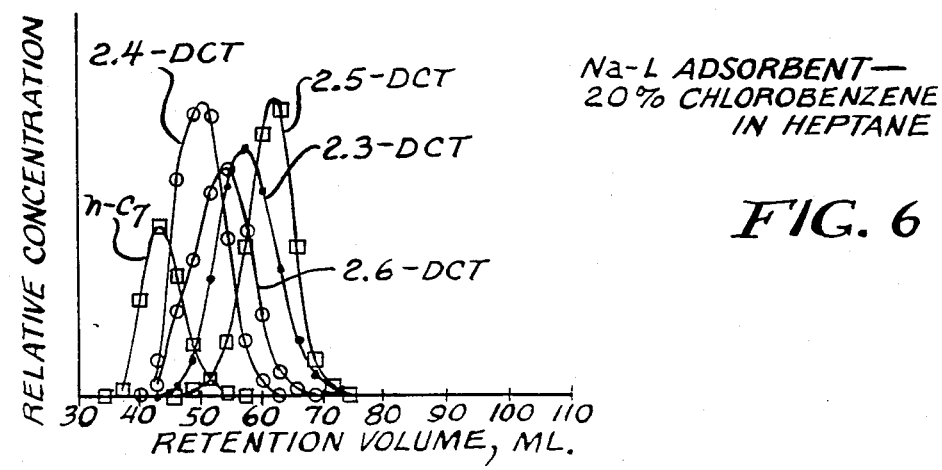
FIG. 6 is a chromatographic trace representing the separation of DCT isomers of Example III with a partially sodium-exchanged K-L zeolite.

| Sample No. | Desorbent | Component | GRV | NRV | BETA ($\beta$) |
|---|---|---|---|---|---|
| II-1 | 50% chlorobenzene | Nonane | 45.2 | 0.0 | tracer |
|  | 50% n-heptane | 2,4-DCT | 47.1 | 1.9 | 2.34 |
|  |  | 2,6-DCT | 49.0 | 3.8 | 1.20 |
|  |  | 2,5-DCT | 49.7 | 4.5 | Reference |
|  |  | 2,3-DCT | 48.8 | 3.6 | 1.26 |
| II-2 | 30% chlorobenzene | Nonane | 44.9 | 0.0 | tracer |
|  | 70% n-heptane | 2,4-DCT | 48.1 | 6.0 | 2.87 |
|  |  | 2,6-DCT | 51.7 | 9.7 | 1.35 |
|  |  | 2,5-DCT | 54.1 | 12.0 | Reference |
|  |  | 2,3-DCT | 51.6 | 9.5 | 1.39 |
| II-3 | 20% chlorobenzene | Nonane | 44.9 | 0.0 | 0.0 |
|  | 80% n-heptane | 2,4-DCT | 48.9 | 4.0 | 2.4 |
|  |  | 2,6-DCT | 53.4 | 8.5 | 1.37 |
|  |  | 2,5-DCT | 56.6 | 11.6 | Reference |
|  |  | 2,3-DCT | 54.9 | 10.0 | 1.17 | were the same as in Example I. The chromatographic tracing obtained is shown in FIG. 6. The results are also presented in the following Table 3.

TABLE 3

| Desorbent | Component | GRV | NRV | BETA ($\beta$) |
|---|---|---|---|---|
| 20% chlorobenzene | Nonane | 43.5 | 0.0 | tracer |
| 80% n-heptane | 2,4-DCT | 49.7 | 6.2 | 2.90 |
|  | 2,6-DCT | 53.2 | 9.7 | 1.86 |
|  | 2,5-DCT | 61.5 | 18.0 | Reference |
|  | 2,3-DCT | 57.4 | 14.0 | 1.29 |

EXAMPLE III

In order to demonstrate the selective adsorption of 2,5-DCT isomer with the preferred sodium exchanged L zeolite adsorbent, an additional pulse test was performed with the feed mixture of Example II, using an L zeolite in which the potassium ions were partially exchanged by sodium ions. Analysis of the partially exchanged zeolite was 2.43% (wt.) Na, 9.27% K., 6.14% L.O.I. at 900° C.

For these pulse tests, the column was filled with 70 cc of the desired adsorbent and maintained at a temperature of 150° C. and a pressure sufficient to maintain liquid-phase operations. The feed mixture employed for each test was the same as in Example II. The desorbent material was 20 vol. % chlorobenzene and 80 vol. % n-heptane. The operations taking place for these tests

EXAMPLE IV

Figure 7:
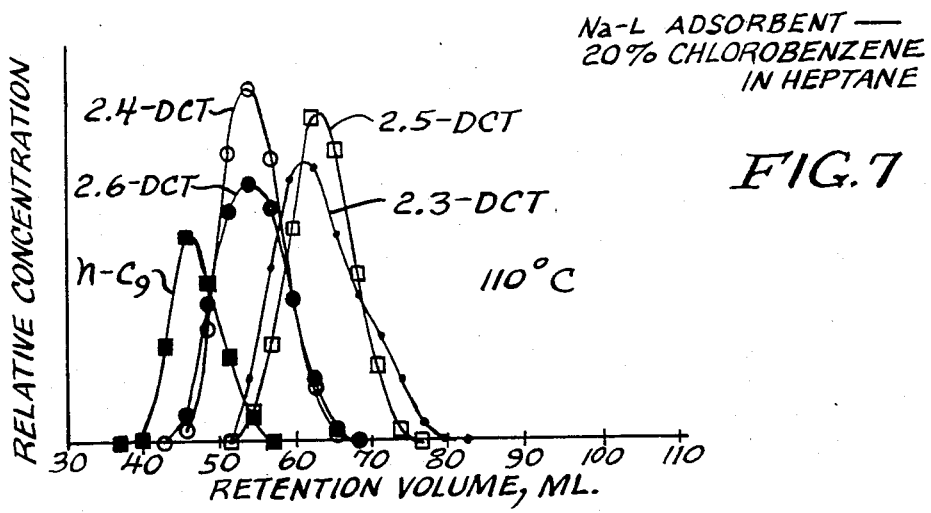
FIGS. 7–9 illustrate the separation of Example IV at different temperatures.
Figure 8:
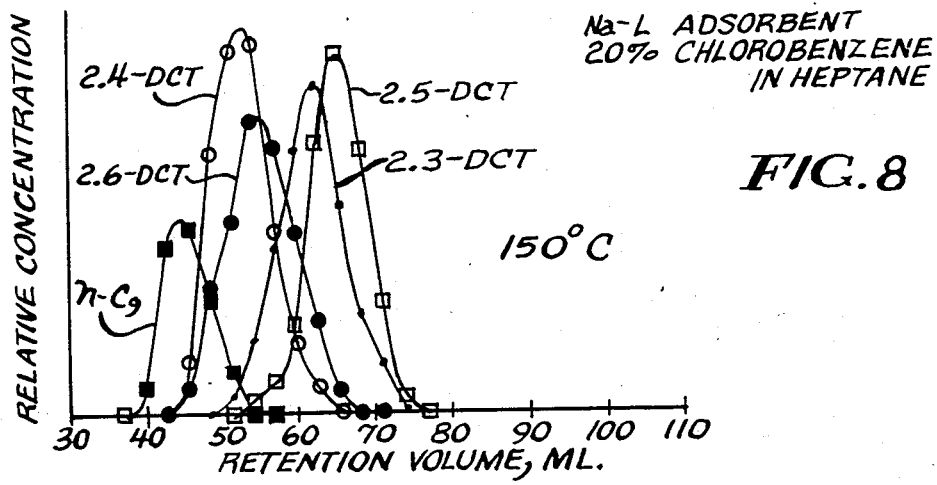
Figure 9:
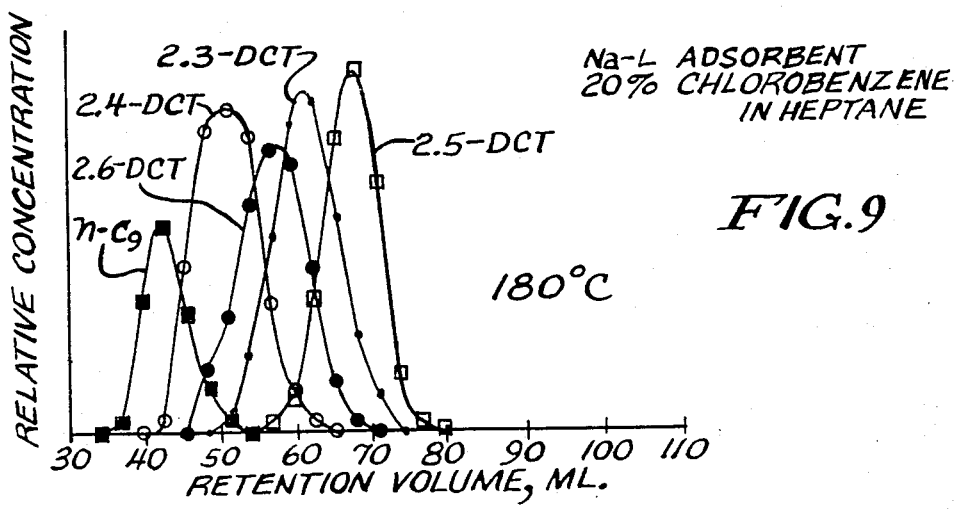

In this experiment, three pulse tests were performed to demonstrate the effect of temperature on the separation of this invention with the L zeolite partially exchanged with sodium that analyzed 1.61% Na, 7.08% K. and 0.55% L.O.I. at 900° C. The conditions, feed, desorbent and method of operation for this experiment were substantially the same as those previously described for Example III, except that temperatures of 110° C., 150° C. and 180° C. were used in Samples IV-1, IV-2 and IV-3, respectively. FIGS. 7, 8 and 9, respectively, contain the tracings from these pulse tests, which show some separation of the components at 110° C., but increasing selectivities at 150° C. and 180° C. The results of the pulse tests are also presented in the following Table 4.

TABLE 4

| Sample No. | Desorbent | Component | GRV | NRV | BETA ($\beta$) |
|---|---|---|---|---|---|
| IV-1 (110° C.) | 20% chlorobenzene | Nonane | 46.6 | 0.0 | tracer |
|  | 80% n-heptane | 2,4-DCT | 54.1 | 7.5 | 2.23 |
|  |  | 2,6-DCT | 54.1 | 7.5 | 2.24 |
|  |  | 2,5-DCT | 63.4 | 16.8 | Reference |
|  |  | 2,3-DCT | 62.4 | 15.8 | 1.06 |
| IV-2 (150° C.) | 20% chlorobenzene | Nonane | 45.1 | 0.0 | tracer |
|  | 80% n-heptane | 2,4-DCT | 52.0 | 6.9 | 2.95 |
|  |  | 2,6-DCT | 55.0 | 9.8 | 2.06 |
|  |  | 2,5-DCT | 65.4 | 20.3 | Reference |

TABLE 4-continued

| Sample No. | Desorbent | Component | GRV | NRV | BETA ($\beta$) |
|---|---|---|---|---|---|
| | | 2,3-DCT | 61.5 | 16.4 | 1.23 |
| IV-3 | 20% chlorobenzene | Nonane | 42.5 | 0.0 | tracer |
| (180° C.) | 80% n-heptane | 2,4-DCT | 50.8 | 8.2 | 3.05 |
| | | 2,6-DCT | 57.4 | 14.9 | 1.69 |
| | | 2,5-DCT | 67.7 | 25.1 | reference |
| | | 2,3-DCT | 61.3 | 18.8 | 1.34 |

EXAMPLE V

An additional pulse test was performed with the same feed and under the same conditions as Example II, using an L zeolite in which the potassium ions were partially exchanged with lithium ions. The zeolite analyzed 0.71% (wt.) Li, 9.55 K., 0.57% L.O.I. at 900° C. The desorbent material was 50% (vol.) chlorobenzene in n-heptane. The results shown in the following Table 5 indicate that separation of 2,5-DCT from 2,6-DCT is satisfactory, but that 2,3-DCT, which is coextracted with 2,5-DCT, must be removed from the extract product by fractionation to obtain pure 2,5-DCT.

TABLE 5

| Component | GRV | NRV | Beta ($\beta$) |
|---|---|---|---|
| Nonane | 46.1 | 0.0 | tracer |
| 2,4-DCT | 46.9 | 0.8 | 2.58 |
| 2,6-DCT | 47.7 | 1.6 | 1.25 |
| 2,5-DCT | 48.1 | 2.0 | Reference |
| 2,3-DCT | 48.0 | 1.9 | 1.05 |

EXAMPLE VI

The pulse test of Example II was repeated except that the desorbent material was 100% 1,2-dichlorobenzene. The results are shown in the following Table 6. The results of Example II suggest that increased selectivity between 2,6-DCT and 2,5-DCT with this adsorbent-/desorbent combination can be obtained by dilution of the desorbent with from 10-50% saturated aliphatic hydrocarbon.

TABLE 6

| Component | GRV | NRV | Beta ($\beta$) |
|---|---|---|---|
| Nonane | 46.5 | 0.0 | tracer |
| 2,4-DCT | 47.7 | 1.2 | 2.78 |
| 2,6-DCT | 49.4 | 3.0 | 1.13 |
| 2,5-DCT | 49.9 | 3.4 | Reference |
| 2,3-DCT | 48.8 | 2.3 | 1.46 |

EXAMPLE VII

Another pulse test was performed on a feed having the following analysis:

| | wt. % |
|---|---|
| 2,4-DCT | 19.2 |
| 2,6-DCT | 7.0 |
| 2,5-DCT | 63.8 |
| 2,3-DCT | 9.6 |
| chlorotoluenes | 0.4 |
| | 100.0 |

The adsorbent was the partially exchanged K-L zeolite of Example IV and the desorbent was 100% chlorobenzene. The column temperature was 150° C. Other conditions were the same as in Example I. The results, set forth in the following Table 7, show that although some 2,3-DCT was coextracted with the 2,5-DCT product, most of the 2,3-DCT can be removed in the raffinate, together with the other DCT isomers in the feed, 2,4- and 2,6-DCT.

TABLE 7

| Component | GRV | NRV | BETA ($\beta$) |
|---|---|---|---|
| n-nonane | 45.9 | 0.0 | tracer |
| 2,4-DCT | 47.4 | 1.4 | 2.26 |
| 2,6-DCT | 47.4 | 1.4 | 2.27 |
| 2,5-DCT | 49.2 | 3.3 | reference |
| 2,3-DCT | 48.8 | 2.8 | 1.15 |

We claim:

1. A process for separating 2,5 dichlorotoluene from feed mixtures of 2,5-dichlorotoluene and at least one other isomer of dichlorotoluene which process comprises contacting said feed mixture at adsorption conditions, with an adsorbent comprising an L-type zeolite at least partially exchanged with sodium or lithium ions at cation exchange sites, selectively adsorbing said 2,5-dichlorotoluene to the substantial exclusion of said other isomers, removing the relatively non-adsorbed portion of the feed mixture from contact with the adsorbent, and thereafter recovering the adsorbed isomer from the adsorbent by contacting said adsorbent, at desorption conditions, with a desorbent.

2. The process of claim 1 wherein said desorbent comprises from 10-50% (vol.) of chlorobenzene and from 90-50% (vol) of a saturated aliphatic hydrocarbon having less than 9 carbon atoms.

3. The process of claim 1 wherein said exchange sites are fully exchanged with sodium.

4. The process of claim 1 wherein said adsorption conditions include a temperature in the range of about 20° C. to about 250° C. and a pressure sufficient to maintain liquid phase.

5. The process of claim 1 wherein said separation is effected by means of a simulated moving bed system.

6. The process of claim 5 wherein the simulated moving bed uses a countercurrent system.

7. The process of claim 5 wherein the simulated moving bed uses a cocurrent system.

8. A process for the separation of dichlorotoluene isomers from a feed mixture comprising said isomers which process comprises contacting said feed mixture, at adsorption conditions, with an adsorbent comprising an L-type zeolite having cations selected from the group consisting of sodium, lithium or potassium and combinations thereof at cation exchange sites, selectively adsorbing one or more of the adsorbable isomers, removing the less strongly adsorbed portion of the feed mixture from contact with the adsorbent and thereafter recovering said adsorbed dichlorotoluene isomers by contacting the dichlorotoluene-containing adsorbent, at desorption conditions, with a desorbent material comprising from 10 to 50% (vol.) chlorobenzene and from 90 to 50% (vol.) of a saturated aliphatic hydrocarbon having less than 9 carbon atoms.

9. The process of claim 7 wherein said aliphatic hydrocarbon comprises n-heptane.

10. The process of claim 2 wherein said less strongly adsorbed portion comprises 2,4-DCT in higher concentration (excluding desorbent) and 2,3- and 2,6-DCT in substantially lower concentrations than in said feed and said adsorbed isomers comprise 2,5-DCT in substantially higher concentration than in said feed.

11. The process of claim 10 wherein said feed contains 2,3-, 2,4-, 2,5- and 2,6-DCT isomers, and said 2,3-DCT is removed from said less strongly adsorbed portion by fractionation following the removal thereof from contact with said first-mentioned adsorbent and contacting the remaining 2,4- and 2,6-DCT isomers of said less strongly adsorbed portion with a second adsorbent from the same group as the first-mentioned adsorbent, removing the less strongly adsorbed portion thereof from contact with said second adsorbent and thereafter recovering 2,6-DCT from said second adsorbent by contacting said second adsorbent at desorption conditions with a second desorbent selected from the same group as the first-mentioned desorbent.

12. The process of claim 11 wherein said first-mentioned and second desorbents are a 20/80 mixture of chlorobenzene/n-heptane.

13. The process of claim 1 wherein said desorbent comprises from 10 to 50% (vol.) chlorobenzene and from 90 to 50% (vol.) of a saturated aliphatic hydrocarbon having less than 9 carbon atoms.

14. The process of claim 1 wherein said desorbent comprises 1,2-dichlorobenzene.

15. The process of claim 9 wherein said adsorbent contains a mixture of potassium and sodium cations at cation exchange sites.

16. The process of claim 2 wherein said aliphatic hydrocarbon comprises n-heptane.

* * * * *